(12) United States Patent
Goldman et al.

(10) Patent No.: US 6,407,081 B1
(45) Date of Patent: Jun. 18, 2002

(54) METHOD FOR INHIBITING CYTOKINE PRODUCTION BY CELLS

(75) Inventors: Michel Goldman, Brussels; Hélène Margery, Bièrges; Patrick Adelin Oscar Robberecht, Brussels; Jean Pierre Robert Tassignon, Brussels; Michel Vandevelde, Brussels, all of (BE)

(73) Assignee: Previsan AG, Zug (CH)

( * ) Notice: Subject to any disclaimer, the term of this patent is extended or adjusted under 35 U.S.C. 154(b) by 0 days.

(21) Appl. No.: 09/555,258

(22) PCT Filed: Nov. 25, 1998

(86) PCT No.: PCT/BE98/00183
§ 371 (c)(1),
(2), (4) Date: Oct. 13, 2000

(87) PCT Pub. No.: WO99/27937
PCT Pub. Date: Jun. 10, 1999

(30) Foreign Application Priority Data

Nov. 26, 1997 (BE) ................................................ 9700949

(51) Int. Cl.$^7$ ............................................. A61K 31/655
(52) U.S. Cl. ....................... 514/149; 514/150; 514/151; 514/579
(58) Field of Search .................. 514/149, 150, 514/151

(56) References Cited
U.S. PATENT DOCUMENTS
5,585,367 A 12/1996 Vandevelde et al.

OTHER PUBLICATIONS

Rice et al., Azodicarbonamide inhibits HIV–1 replication by targeting the nucleocapsid protein (Mar. 1997) Nature Medicine, vol. 3, No. 3, pp. 341–345.

De Wit et al., The inhection of deaggregated gamma globulins in adult mice induces antigen–specific unresponsiveness of T helper type 1 but not type 2 lymphocytes (Jan. 1992) J. Exp. Med., vol. 175, pp. 9–14.

STN Registry (Apr. 2001) Diamide structure and other names.

J. Tassignon et al., "Azodicarbonamide Inhibits T–cell Responses in Vitro and in Vivo" in Nature Medicine, vol. 5, No. 8, Aug. 1999, pp. 947–950.

*Primary Examiner*—Leon B. Lankford, Jr.
(74) *Attorney, Agent, or Firm*—Dykema Gossett PLLC

(57) ABSTRACT

The invention concerns a method for inhibiting cytokine production by cells, in particular animal or human cells, and their secretion, which consists in applying on said cells at least an azo compound derivatives corresponding to formula (I), in which A represents a carboxyl or a group (a); B represents a carboxyl or a group (b); $R^1$, $R^2$, $R^3$ and $R^4$=H, Hal, OH or a hydrocarbon radical, $R^1$ and $R^2$ as well as $R^3$ and $R^4$ capable of being a heterocyclic ring; $X^1$ and $X^2$=O or $NR^5$, where $R^5$=H, Hal, a hydrocarbon radical or a nitro group.

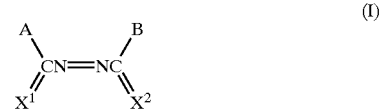

13 Claims, 2 Drawing Sheets

METHOD FOR INHIBITING CYTOKINE PRODUCTION BY CELLS

Figure 1:
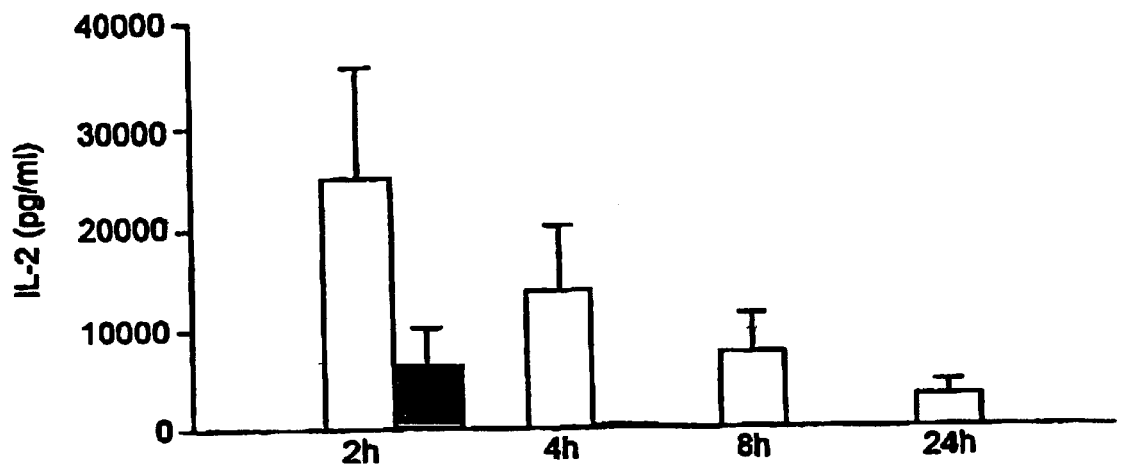

This application is a U.S. national phase of PCT/BE98/00183, filed Nov. 25, 1998, which claims priority of Belgium Application Serial No. 9700949, filed Nov. 26, 1997.

The present invention relates to a process for in vitro inhibition of the production of cytokines by cells, in particular animal or human cells, and of the secretion thereof.

The object of the present invention is to provide a process for in vitro inhibition of the production of cytokines which does not jeopardise said cells. Advantageously, this process will allow inhibition of the production and secretion of substances promoting the appearance of immunoallergic phenomena in these cells.

This object is achieved according to the invention by a process as described above comprising application onto said cells of at least one azo derivative of the formula

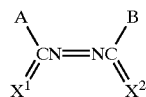

in which A represents a carboxyl group or a group

B represents a carboxyl group or a group

$R^1$, $R^2$, $R^3$ and $R^4$ are identical or different and each mutually independently represent a hydrogen or halogen atom, an optionally substituted aliphatic or aromatic hydrocarbon residue or a hydroxy group, $R^1$ and $R^2$ possibly being joined together to form a heterocyclic nucleus with the nitrogen atom adjacent thereto, and $R^3$ and $R^4$ possibly being joined together to form a heterocyclic nucleus with the nitrogen atom adjacent thereto, $X^1$ and $X^2$ are identical or different and each mutually independently represent an oxygen atom or a group $NR^5$, in which $R^5$ is a hydrogen or halogen atom, an optionally substituted aliphatic or aromatic hydrocarbon residue or a nitro group, and in which, when two groups $NR^5$ are simultaneously present, each $R^5$ may be identical to or different from the other, together with the salts, esters and isomers thereof.

Various of these azo derivatives are compounds which are known in particular for the antiviral activity thereof, especially against viruses of the retrovirus group, in particular the AIDS virus (c.f. WO-A-9116054 and WO-A-9107876, together with U.S. Pat. No. 5,585,367).

More particularly in relation to 1,1'-azobisdimethylformamide, which is also known as diamide, many researchers have studied the activation phenomenon of the intracellular transcription factor NF-kappaB and have demonstrated that diamide blocks the function of certain enzymes in the activation cascade for this factor.

Other authors have demonstrated that at certain concentrations diamide induces apoptosis in certain cell lines.

Still other authors have demonstrated that diamide has an effect on certain membrane receptors.

However, none of these studies reveals any inhibitory action of diamide on the production of cytokines by the cells under observation. It may even be noted that C. Mendez et al. in "Oxidants augment endotoxin-induced activation of alveolar macrophages", SHOGK, volume 6, no. 3, pp. 157–163, 1996, observe an insignificant increase in the production of tumour necrosis factor at a dose of 1 mmol, i.e. the reverse effect to that repeatedly observed on various cytokines according to the present invention.

It is moreover known that the azo derivatives according to the invention exhibit extremely low intrinsic toxicity towards the human body or healthy cells which are treated.

According to one embodiment of the invention, the process comprises in vitro inhibition of the production and secretion of interleukins by cells. Interleukins which may in particular be mentioned are interleukins IL-2, IL-4, IL-5, IL-6, IL-8, IL-10, IL-12 and IL-15, with inhibition of IL-2 and IL-5 most particularly being intended.

According to another embodiment of the invention, the process comprises in vitro inhibition of the production and secretion of interferon-γ (IFN-γ) by cells. According to still another embodiment, the process comprises inhibition of the production and secretion of tumour necrosis factor α (TNF-α).

According to an advantageous embodiment of the invention, in the above-stated general formula, $R_1$ to $R_5$ each represent an aliphatic or aromatic hydrocarbon residue comprising 1 to 6 carbon atoms. The heterocycles optionally formed in the general formula may contain, apart from one nitrogen atom, at least one other heteroatom, for example oxygen. The heterocycle is, for example, pentagonal to octagonal, preferably being hexagonal. The azo derivative according to the invention may be selected from among the group comprising azobisformamidine derivatives, such as 1,1'-azobisform-amidine, 1,1-azobisnitroformamidine, 2,2'-azobismethyl-formamidine, 1,1'-azobisfluoroformamidine, 1-monochloro-azobisformamidine, azobis[chloroformamidine], azobisformamide derivatives, such as 1,1'-azobisformamide and dimethylazobisformamide, 1,1'-(azodicarbonyl)-dipiperidine, 1,1'-(azodicarbonyl) dimorpholine, azodihydroxamic acid and the salts thereof, azodicarboxylic acid and the salts thereof.

The process advantageously comprises application of the azo derivative onto the cells at a dose which does not induce apoptosis thereof. A micromolar concentration of approx. 0.4 to approx. 200, preferably of 2 to 20, advantageously of 2 to 10, may be considered.

It this regard, 1,1'-azobisdimethylformamide, also known as diamide, may under certain circumstances exhibit the disadvantage of bringing about cellular apoptosis at certain excessively high concentrations, while providing a relatively short half-life of only a few minutes.

According to one embodiment of the invention, at least one of the stated azo derivatives is applied onto cells isolated from macroorganisms or cells of microorganisms, for example originating from cell cultures. The treated cells may also be those from an organ or multicellular tissue taken from the body of a human or an animal, such as for example the cells from a sample of blood or lymph.

According to one embodiment of the invention, at least one of the stated azo derivatives is applied, for example, onto cytokine producing cells isolated from human blood. These cells may be extracted in an overall manner, in which case overall effects will be observed on the various types of lymphocytes, on cells having antigens and on macrophages in co-cultures. A more advanced stage of the investigation may consist in measuring the production of cytokines by highly purified cell lines, for example CD4 lymphocytes.

The cell lines concerned may also be treated by administering azo derivatives to living organisms, including human beings, and measuring the various groups of cytokines in the biological fluids taken from the body of a human or an animal before, during and/or after treatment, and by measuring the production capacity for the lymphokines under consideration after extraction of the cells present in these fluids.

It is also possible to consider treating grafts or cellular tissues, prior to the transplantation thereof into the body of a human or an animal, with an azo derivative according to the invention.

It is also possible to provide the use of pharmaceutical preparations based on azo derivatives according to the invention to treat patients against graft rejection.

Cytokines are produced in the body by different cell reservoirs.

It is known, for example, that lymphocytes specialise specifically in the production of cytokines and that, depending upon the type of cytokine produced, a distinction is drawn between Th1 and Th2 CD4 lymphocytes.

Cytokines are also produced not only by CD8 lymphocytes (IL-4 and IL-5), but also by mast cells and eosinophils and, during uterine implantation, by the ectodermal cells of the trophoblast.

Cytokines are produced by these various cell reservoirs during the appearance of various inflammatory and allergic reactions in general and during the phenomenon of graft rejection. The following is a non-exhaustive list of pathological conditions which may inter alia be mentioned: asthma, atopic dermatitis, allergic seasonal rhinitis, psoriasis, pemphigus, thyroiditis, myasthenia gravis, rheumatoid arthritis, IgA nephropathy, scleroderma, lupus erythematosus, insulin-dependent diabetes, disseminated sclerosis, inflammatory diseases of the digestive tract, Crohn's disease, hypereosinophilia, eosinophilic syndrome, and any condition due to IL-5 mediated cellular apoptosis.

The active substance according to the invention may be applied onto cells alone or mixed with other substances according to the invention, or also mixed with other substances having a different effect on the cells. The active substance(s) may also be applied as such or in the form of a composition comprising at least one of the azo derivatives according to the above-stated formula and an appropriate carrier or vehicle.

Certain compounds according to the invention have at least one asymmetrical C atom and consequently all isomers, including diastereomers and rotational isomers or enantiomers, are also provided by the invention. The invention includes the D and L isomers in pure or mixed form, including racemic mixtures.

Certain acid-type compounds, for example carboxylic acids, may form salts, for example with metals, or with acceptable amines, or esters with compatible alcohols.

The present invention also relates to the use of at least one of the derivatives of the above-stated formula, together with the salts and isomers thereof, for the production of pharmaceutical preparations for use in the treatment or prevention of human or animal conditions arising from pathological cellular production of said cytokines. It is in particular possible to provide the production of pharmaceutical preparations for the treatment and/or prevention of autoimmune and/or inflammatory conditions involving T lymphocytes, allergic inflammatory diseases or also the rejection of allografted and/or xenografted organs and the graft-versus-host reaction after a cellular allograft. Said use will thus advantageously be provided for producing pharmaceutical preparations intended for use in the treatment or prevention of conditions such as those stated above.

The pharmaceutical preparation produced according to the invention may be administered by any appropriate route, inter alia orally, sublingually, rectally or vaginally, by injection or perfusion, locally, transcutaneously or via the mucous membranes. The pharmaceutical preparation contains a therapeutically effective quantity of the above-stated azo derivative(s). Dosage will vary from individual to individual depending upon their own immunological characteristics, which are in part genetically determined. The pharmaceutical preparation may be presented as any appropriate dosage form, for example as capsules, pills, tablets, coated tablets, powders, injectable forms, creams, ointments, known transdermal administration systems, inhalable preparations.

The pharmaceutical formulations and compositions may contain conventional pharmaceutically acceptable excipients, optionally together with conventional pharmaceutical additives. These excipients and additives in particular comprise compatible inert fillers, binders, disintegration agents, buffers, preservatives, antioxidants, lubricants, flavouring agents, thickeners, colours, emulsifiers etc.

Since the primary application is therapeutic, the present invention also provides azo derivatives of the above-stated general formula in which at least one of the groups A and B represents a carboxyl group, together with the pharmaceutically acceptable salts, esters and isomers thereof, for the application thereof as therapeutically active substances. Derivatives of this type which may in particular be considered are azodicarboxylic acids of the following formula

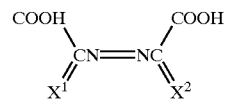

and the salts, esters and isomers thereof.

Similarly, the present invention also relates to azo derivatives of the above-stated general formula, in which the group A represents the group

one of the residues $R^1$ and $R^2$ representing a hydroxy group and the other a hydrogen atom, and in which the group B may simultaneously represent the group

one of the residues $R^3$ and $R^4$ possibly representing a hydroxy group and the other a hydrogen atom, together with the pharmaceutically acceptable salts, esters and isomers thereof, for the application thereof as therapeutically active substances. We have in mind in particular the azodihydroxamic acid of the following formula

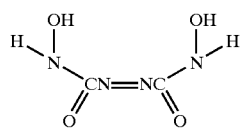

and the salts and isomers thereof.

The invention finally furthermore relates to 1,1'-(azodicarbonyl)dimorpholine of the formula

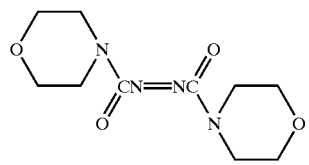

together with the salts, esters and isomers thereof, for the application thereof as therapeutically active substances.

The invention also relates to products containing at least one of the azo derivatives of the above-stated formula and the isomers thereof and at least one cytokine as a combination product for use simultaneously, separately or in a staggered manner in the therapy or prevention of human or animal conditions arising from pathological cellular production of at least one cytokine differing from said cytokine, at least one of which is present in the combination product, or in the therapy or prevention of human conditions, a side effect of which is pathological cellular production of at least one cytokine differing from said cytokine, at least one of which is present in the combination product.

Further embodiments and developments of the invention are stated in the attached claims.

The following Examples are intended to explain the invention in greater detail in an illustrative, non-limiting manner.

The experiments described in these Examples were performed at the Laboratoire d' Immunologie Expérimentale of the Université Libre de Bruxelles, with the exception of Example 7, which was performed in the laboratories of the company UCB S.A.

EXAMPLE 1

Effect of ADA on the Production of IL-5

Peripheral mononuclear blood cells (PMBC) from five healthy human donors are isolated in the conventional manner from 50 ml of their blood and then purified by density gradient centrifugation (Lymphoprep). The cells ($5.10^6$ cells/ml) are activated by 0.3 µg/ml of phytohaemagglutinin (PHA) and cultured for 72 hours at 37° C. in the presence of various concentrations of ADA (20, 10, 5, 1, 0.2 and 0.04 µg/ml). The culture medium consists of RPMI 1640 complemented with 10% foetal calf serum and glutamine and contains mercaptoethanol. The ADA solutions are prepared in dimethyl sulfoxide (DMSO), the working concentration of DMSO during the experiments being 0.1%. Said experiments are performed on 96 well plates (200 µl/well) and, once the plates have been centrifuged at 1500 revolutions per minute for 10 minutes, the supernatants are harvested and the IL-5 content thereof analysed by an ELISA immunoenzymatic assay.

The results of this experiment are shown in Table 1 below.

TABLE 1

| ADA concentration (µg/ml) | IL-5 content as a percentage of the control | | | | | | |
|---|---|---|---|---|---|---|---|
| | 0 | 0.04 | 0.2 | 1 | 5 | 10 | 20 |
| Donor 1 | 100 | 83 | 54 | 48 | 44 | 29 | 9 |
| Donor 2 | 100 | 50 | 42 | 29 | 2 | 2 | 2 |
| Donor 3 | 100 | 58 | 63 | 57 | 23 | 28 | 26 |
| Donor 4 | 100 | 46 | 57 | 37 | 31 | 14 | 5 |
| Donor 5 | 100 | 55 | 58 | 49 | 34 | 31 | 7 |
| Mean | 100 | 58 | 55 | 44 | 27 | 21 | 10 |

These results show that, in comparison with the untreated cells, the PBMC from the five donors tested produce less IL-5 in the presence of ADA. On average, production of IL-5 is 90% inhibited at 20 µg/ml of ADA, 80% at 10 µg/ml and 45% at 0.2 µg/ml.

It should be noted that this is the first time that any effect of ADA has completely surprisingly been revealed at such low concentrations.

Comparable tests were performed in the absence of mercaptoethanol with relatively similar results.

EXAMPLE 2

Effect of ADA on the Production of Interferon-γ

Starting from the same cell cultures as those used in Example 1, the presence of interferon-γ was investigated after treatment with the stated concentrations of ADA. In this case too, inhibition is observed in 4 out of 5 donors, as is shown in Table 2 below.

TABLE 2

| ADA concentration (µg/ml) | Interferon-γ content as a percentage of the control | | | | | | |
|---|---|---|---|---|---|---|---|
| | 0 | 0.04 | 0.2 | 1 | 5 | 10 | 20 |
| Donor 1 | 100 | 62 | 112 | 87 | 68 | 23 | 21 |
| Donor 2 | 100 | 53 | 111 | 98 | 128 | 169 | 86 |
| Donor 3 | 100 | 99 | 70 | 49 | 62 | 43 | 40 |
| Donor 4 | 100 | 82 | — | — | 57 | — | 25 |
| Donor 5 | 100 | 38 | — | — | 25 | — | 16 |
| Mean | 100 | 67 | 98 | 78 | 68 | 78 | 38 |

In these two Examples, the reduction in the production of cytokines is dependent upon the quantity of ADA used (dose dependent effect) and the reduction is observed at concentrations of ADA which cause no cytotoxic effects.

EXAMPLE 3

Effect of ADA on the Production of IL-2, IL-5 and Interferon-γ by Purified T Lymphocytes PBMC from three healthy donors are purified by density gradient chromatography (LymphoPrep). The T lymphocytes are obtained from $15.10^6$ PBMC incubated for 20 to 30 minutes in a waterbath at 37° C. with 0.8 ml of a mixture of LymphoKwik® (One Lambda, Inc., CA, USA). This latter substance is a mixture of complement and specific antibody for antigen units of the cell membrane which lyses the unwanted cells (B lymphocytes, monocytes, etc.). The cells are centrifuged and then washed twice. FACS analysis reveals that the resultant T lymphocyte cultures contain more than 85% of CD3+ cells.

These cultures are treated with various concentrations of ADA. The results are given in Table 3 below.

TABLE 3

| ADA concentration (μg/ml) in % relative to control | 0 | 1 | 5 | 10 | 20 |
|---|---|---|---|---|---|
| IL-2 (mean of 2 donors) | 100 | 68 | 27 | 9 | 3 |
| IL-5 (mean of 2 donors) | 100 | 67 | 60 | 40 | 16 |
| IFN-γ (mean of 3 donors) | 100 | 82 | 34 | 14 | 4 |

EXAMPLE 4

Effect of ADA on the Production of IL-2, IL-5 and Interferon-γ by Purified CD4 T Lymphocytes Purified CD4 T lymphocytes (90% purity) stimulated by PMA (phorbol myristate acetate)+anti-CD28 antibodies from healthy donors are treated with various concentrations of ADA. The results are shown in Table 4 below.

TABLE 4

| ADA concentration (μg/ml) in % relative to control | 0 | 1 | 5 | 10 | 20 |
|---|---|---|---|---|---|
| IL-2 (mean of 2 donors) | 100 | 82 | 30 | 18 | 10 |
| IL-5 (1 donor) | 100 | 69 | 45 | 43 | 38 |
| IFN-γ (mean of 2 donors) | 100 | 73 | 36 | 15 | 12 |
| TNF-α (5 donors) | 100 | 90 | 48 | 32 | 14 |

In Examples 3 and 4, the results are stated as a percentage taking the medium without ADA as 100%. The concentrations corresponding to 100% are respectively 90,000 pg/ml for IL-2, 1100 pg/ml for IL-5, 1900 pg/ml for IFN-γ and 2870 pg/ml for TNF-α. The results are the mean of independent ELISA assays.

It may be noted that, for these donors, the production of IL-5, interferon-γ and TNF-α is inhibited at a concentration of 20 μg/ml of ADA. Even lower concentrations inhibit the secretion of IL-2 by lymphocytes.

It may be concluded from these experiments that ADA acts upon the production and secretion of cytokines in a surprising manner at concentrations very much lower than those required for this substance to have any action against the proliferation of HIV retroviruses in cells and against the proliferation of cancer-type cells, which means that its use may be considered, without toxicity problems, in a hitherto unexpected therapeutic area.

EXAMPLE 5

Effect of ADA on the in vivo Production of Cytokines

A single intraparenteral injection of azodicarbon-amide (ADA) at a dose of 100 mg/kg bodyweight or corresponding carrier is made into BALB/C mice (Harlan, Zeist, Netherlands) one day before intraparenteral inoculation of 25 μg of hamster 145-2C11 mAb, an anti-mouse $CD_3$ mAb which brings about massive in vivo activation of polyclonal T cells, resulting in systemic cytokine release. Sera are collected 2, 4, 8 and 24 hours after the anti-$CD_3$ treatment and the cytokine (IL-2, IL-4) levels are determined by an ELISA test (Genzyme).

Figure 2:
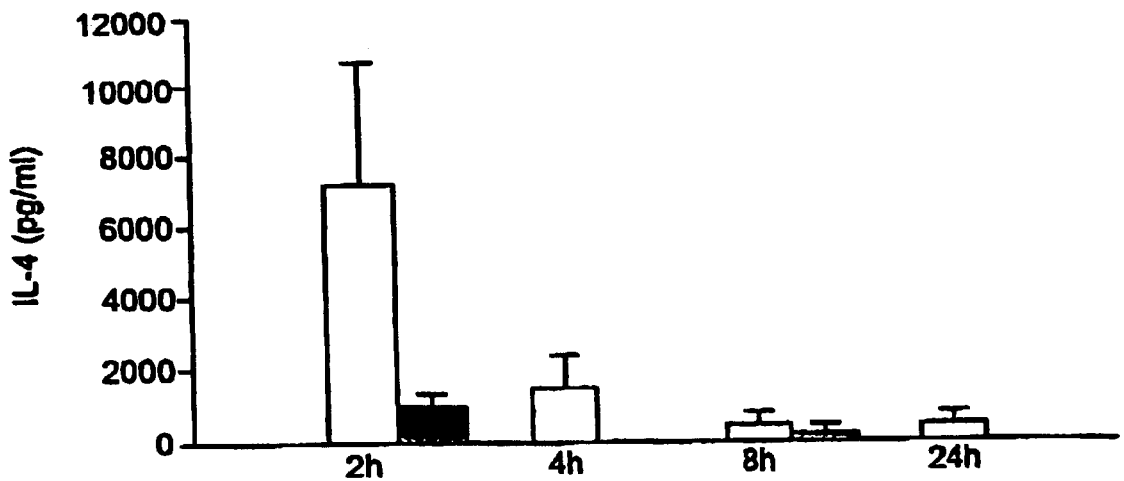

FIGS. 1 and 2 are graphs showing, on the y-axis, the quantities of IL-2 and IL-4 in the serum as a mean of 5 test animals. The x-axis shows the times at which blood was sampled. The empty bars show the results obtained with the carrier and the shaded bars show those obtained with prior ADA treatment.

It is clear from this test and FIGS. 1 and 2 which illustrate it that treatment with ADA brings about a significant reduction in the release of interleukins IL-2 and IL-4 after injection of 145-2C11 mAb into mice.

EXAMPLE 6

Effect of ADA on Allograft Rejection

Skin grafts, which are well known to be highly dependent upon T cells, are prepared from the tails of four female C57BL/6. CH-$2^{bm12}$ mice (Jackson Laboratory, Bar Harbor, Me., USA). These grafts are grafted onto the sides of C57BL/6 mice (Harlan, Zeist, Netherlands). A dressing is applied around the hole. This dressing is removed 10 days later and the grafts are inspected daily. The test mice receive a daily intraparenteral injection of 50 mg/kg bodyweight of ADA and the controls receive an equivalent quantity of the corresponding carrier until acute rejection is observed.

Figure 3:
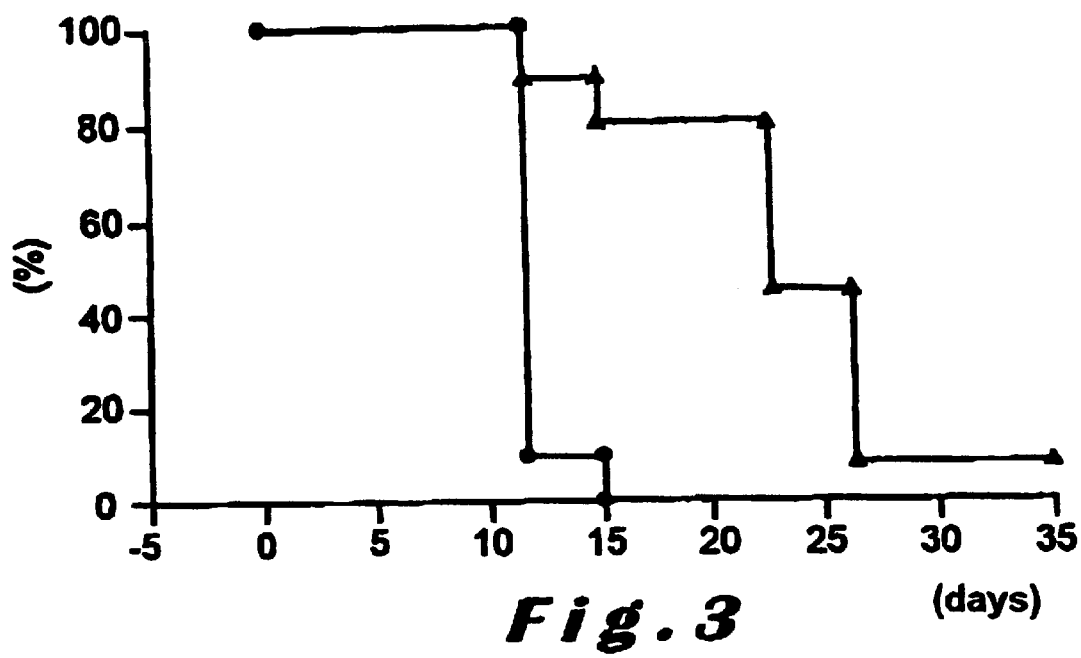

On the graph in FIG. 3, survival of the skin graft is plotted, in %, on the y-axis, while the number of days since the transplant is plotted on the x-axis.

It may be noted that rejection of the skin allograft was significantly delayed in the mice treated with ADA (black triangles) in comparison with the control (black circles), which confirms that ADA also exerts a suppressive action on T cells in vivo.

EXAMPLE 7

200 ml of blood are taken and heparinised from healthy male and female volunteers. Mononuclear cells are isolated by Ficoll-Hypaque centrifugation and resuspended in a medium consisting of RPMI 1640 complemented by 5% autologous serum, 1 mN of glutamine, 1001 IU/ml of penicillin, 10 μg/ml of streptomycin, 10 μg/ml of phyto-haemagglutinin (PHA), 10 μg/ml of phorbol myristate acetate (PMA) and test compounds as stated per individual experiment at a cellular density of 2,000,000 per ml. The cells are distributed in 96 well microtitre plates in 250 μl portions per well and incubated for 48 hours at 37° C. The supernatants are then harvested and the IL-2 and IL-5 concentrations quantified by a standard ELISA assay using a biotin/streptavidin system. By way of variant, PHA was replaced with 0.1 μg/ml of monoclonal antibodies directed against human CD3 in order to achieve more specific activation of the T cells.

TABLE 5

| Test compounds | No. of tests | IL-2 inhibition (%) | | IL-5 inhibition (%) | |
|---|---|---|---|---|---|
| | | 10 μM | 32 μM | 10 μM | 32 μM |
| A | 9 | 3 | 28 | 12 | 29 |
| B | 6 | 0.2 | 11 | 17 | 39 |
| C | 5 | 6 | 9 | 37 | 51 |

A = diamide
B = 1,1'-(azodicarbonyl)dipiperidine
C = 1,1'-(azodicarbonyl)dimorpholine

EXAMPLE 8

Effect of ADA on in vivo Production of Interferon-γ

Brown-Norway rats are actively sensitised with 5% ovalbumin in 0.9% NaCl. 24 hours later, bronchial reactivity to metacholine is measured on the anaesthetised rats. Immediately measurement of bronchial reactivity is complete, splenocytes are taken from these rats and cultured to determine IFN-γ production by these cells.

ADA is administered 24 hours before the beginning of the ovalbumin sensitisation phase and daily throughout the duration of the test, except for the days of the measurements. The ADA is administered orally in suspension in 1% methylcellulose at a twice daily dosage of 500 mg/kg and 1000 mg/kg bodyweight.

Figure 4:
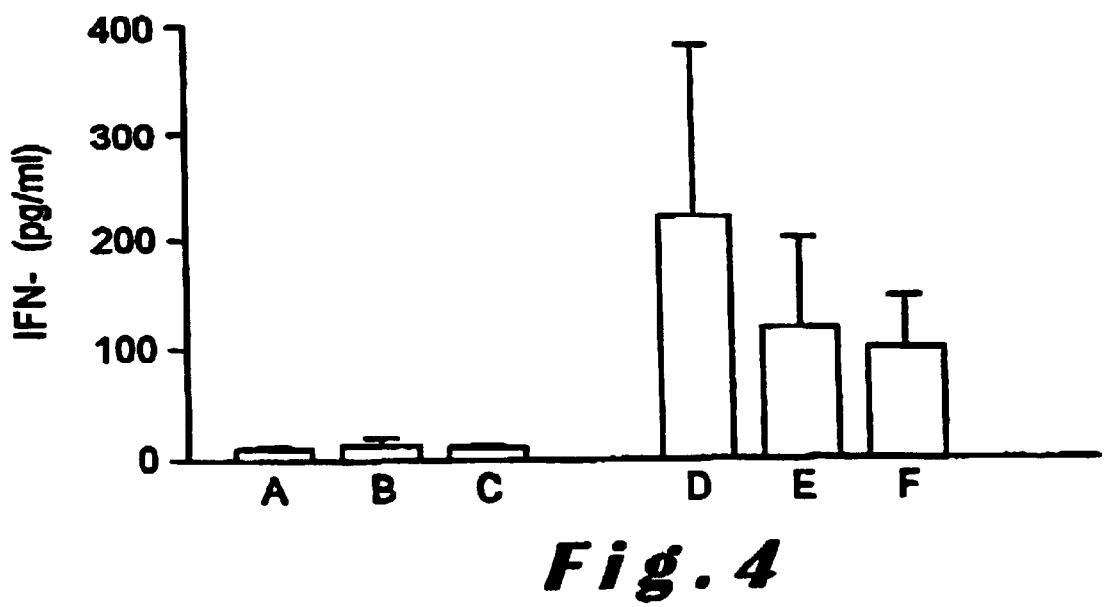

The results are shown in FIG. 4. The quantities of IFN-γ are plotted on the y-axis in pg/mg of protein. On the x-axis, the empty bars A to F correspond to the following experiments:

A—no stimulation with ovalbumin, no active substance

B—no stimulation with ovalbumin, ADA orally, 500 mg/kg

C—no stimulation with ovalbumin, ADA orally, 1000 mg/kg

D—stimulation with ovalbumin, no active substance

E—stimulation with ovalbumin, ADA orally, 500 mg/kg

F—stimulation with ovalbumin, ADA orally, 1000 mg/kg

It is clearly evident from this test that ADA has an inhibitory effect on the production of INF-γ by splenocytes in rats treated to exhibit elevated bronchial reactivity.

EXAMPLE 9

Capsules for Oral Administration

Composition of One Capsule:

500 mg of ADA 10 mg of glycerol monostearate 10 mg of precipitated silicon dioxide 5 mg of magnesium stearate.

This composition is filled into gelatine capsules in conventional manner. Capsules may, for example, be administered with a rising dosage (max. 100 mg/kg/day) to patients receiving a kidney transplant or other allograft (heart, lung, liver etc.) at the latest for the 72 hours preceding the transplant in order to diminish or suppress the acute rejection phase. Frequent monitoring of IL-2 production by the patients is advisable. The capsules will be administered alone or in association with cyclosporin and corticosteroids or any other appropriate immunosuppressant treatment.

EXAMPLE 10

Coated Tablets

Tablets containing 250 mg of azobisformamidine are produced in the conventional manner using the following excipients: hydroxypropylmethylcellulose, hydroxypropylcellulose, titanium dioxide, polyethylene glycol 400, black iron oxide.

These tablets may be administered to achieve an adequate reduction in IgE production due to the reduction in IL-5 in allergic reactions (seasonal allergic rhinitis, for example). This treatment will be performed to achieve and maintain remission.

EXAMPLE 11

Injectable Dosage Form

An injectable dosage form is prepared on the basis of 1 g of dimethylazobisformamide and pyrogen-free distilled water with added NaCl.

These dosage forms should be administered, for example, during acute upsurges in production of autoantibodies (autoimmune conditions, lupus erythematosus, autoimmune diabetes, autoimmune thyroiditis etc.) while bearing in mind that improvement is usually observed after a period of 6 to 8 weeks.

EXAMPLE 12

Cream or Ointment

A cream or ointment is prepared with 1,1'-azobis-[chloroformamidinel] (chloroazodin) and, as excipient, in particular glycerol, paraffin oil, petroleum jelly.

This cream may be applied locally as an immunomodulator in scleroderma.

EXAMPLE 13

Transdermal administration systems may also be provided for dimethylazobisformamide.

These systems may be applied in such a manner as to bring about a sustained reduction in circulating lymphokines in patients suffering from asthma which is difficult to control.

This treatment may be combined with the use of conventional treatments.

EXAMPLE 14

Tablets for Oral Administration

Composition of One Tablet:

100 mg of ADA 10 mg of glycerol monostearate 10 mg of precipitated silicon dioxide 5 mg of magnesium stearate.

This composition is introduced in conventional manner into a tabletting machine.

IL-2 may be administered to a patient, for example during cancer treatment. The excess levels of IL-2 in the body of the patient treated in this manner stimulate overproduction of other cytokines, in particular IL-5, by the patient's cells, which causes side-effects, such as pemphigus, thyroiditis, rheumatoid arthritis, Crohn's disease, scleroderma, hypereosinophilia etc.

It is thus possible to combine administration of IL-2 with regular doses of ADA tablets to counteract these side-effects.

IL-2 and ADA may be administered simultaneously, separately or in a staggered manner.

It should be understood that the present invention is not limited in any manner to the above-stated embodiments and developments and that considerable modification may be made without extending beyond the scope of the attached claims.

What is claimed is:

1. Method for the therapeutic treatment of an animal body against pathological cellular production of cytokines, not relating to viral diseases, comprising the administration of a therapeutically effective quantity of an active substance to said animal body, this active substance being selected from among one or more azo derivatives of the formula

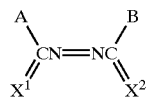

in which A represents a carboxyl group or a group

B represents a carboxyl group or a group

$R^1$, $R^2$, $R^3$ and $R^4$ are identical or different and each mutually independently represent a hydrogen or halogen atom, an optionally substituted aliphatic or aromatic hydrocarbon residue or a hydroxy group, $R^1$ and $R^2$ being non-joined or joined together to form a heterocyclic nucleus with the nitrogen atom adjacent thereto, and $R^3$ and $R^4$ being non-joined or joined together to form a heterocyclic nucleus with the nitrogen atom adjacent thereto, $X^1$ and $X^2$ are identical or different and each mutually independently represent an oxygen atom or a group $NR^5$, in which $R^5$ is a hydrogen or halogen atom, an optionally substituted aliphatic or aromatic hydrocarbon residue or nitro group, and in which, when two groups $NR^5$ are simultaneously present, each $R^5$ may be identical to or different from the other, together with the salts, esters and isomers thereof.

2. Process according to claim 1, characterised in that it comprises inhibition of the production and secretion of interleukins.

3. Process according to claim 1, characterised in that it comprises inhibition of the production and secretion of a cyktoine selected from the group consisting of interferon γ and tumour necrosis factor α.

4. Process according to claim 1, characterised in that $R^1$ to $R^5$ each represent an aliphatic or aromatic hydrocarbon residue comprising 1 to 6 carbon atoms.

5. Process according to claim 1, characterised in that the azo derivative is selected from the group consisting of azobisformamidine derivatives, azobisformamide derivatives, 1,1'-(azodicarbonyl)dipiperidine, 1,1'-(azodicarbonyl)-dimorpholine, azodihydroxamic acid and the salts thereof, and azodicarboxylic acid and the salts thereof.

6. Process according to claim 1, characterised in that it comprises said application of a composition comprising at least one of said azo derivatives and an appropriate carrier.

7. Process according to claim 5, wherein said azobisformamidine derivatives are selected from the group consisting of azobisformamidine derivatives such as 1,1'-azobisformamidine, 1,1-azobinistroformamidine, 2,2'-azobismethylformamidine, 1,1'-azobisfluoroformamidine, 1-mono-chloroazobisformamidine, azobis.

8. Process according to claim 5, wherein said azobisformamide derivatives are selected from the group consisting of 1,1'-azobisformamide and dimethylazobisformamide.

9. Method for the preventive treatment of an animal body against an expected pathological cellular production of cytokines, not relating to viral diseases, comprising the administration of a therapeutically effective quantity of an active substance to said animal body, this active substance being selected from among one or more azo derivatives of the formula

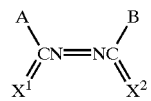

in which A represents a carboxyl group or a group

B represents a carboxyl group or a group

$R^1$, $R^2$, $R^3$ and $R^4$ are identical or different and each mutually independently represent a hydrogen or halogen atom, an optionally substituted aliphatic or aromatic hydrocarbon residue or a hydroxy group, $R^1$ and $R^2$ being non-joined or joined together to form a heterocyclic nucleus with the nitrogen atom adjacent thereto, and $R^3$ and $R^4$ being non-joined or joined together to form a heterocyclic nucleus with the nitrogen atom adjacent thereto, $X^1$ and $X^2$ are identical or different and each mutually independently represent an oxygen atom or a group $NR^5$, in which $R^5$ is a hydrogen or halogen atom, an optionally substituted aliphatic or aromatic hydrocarbon residue or nitro group, and in which, when two groups $NR^5$ are simultaneously present, each $R^5$ may be identical to or different from the other, together with the salts, esters and isomers thereof.

10. Method according to claim 9, wherein said animal body is a human body.

11. Method according to claim 9, wherein said animal body is to receive a graft in a grafting procedure, and wherein said therapeutically-effective quantity of said active substance is administered to said animal body at least 72 hours prior to said grafting procedure.

12. Method according to claim 9, wherein said therapeutically-effective quantity of said active substance is administered to said animal body one day before the expected pathological cellular production of cytokines.

13. Method according to claim 1, wherein said animal body is a human body.

* * * * *